United States Patent
Eldreth

[11] Patent Number: 5,924,866
[45] Date of Patent: *Jul. 20, 1999

[54] SALIVA EJECTOR BITE BLOCK

[76] Inventor: Mary Anne Eldreth, 3820 La Vista Cir., Jacksonville, Fla. 32217

[*] Notice: This patent is subject to a terminal disclaimer.

[21] Appl. No.: 09/019,623

[22] Filed: Feb. 6, 1998

Related U.S. Application Data

[63] Continuation-in-part of application No. 08/805,135, Feb. 24, 1997, Pat. No. 5,769,635.

[51] Int. Cl.$^6$ ...................................................... A61C 5/00
[52] U.S. Cl. ............................. 433/140; 433/93; 600/238
[58] Field of Search ............................ 433/93, 138, 140; 600/238; 128/862

[56] References Cited

U.S. PATENT DOCUMENTS

| | | | |
|---|---|---|---|
| 323,627 | 8/1885 | Brickford | 600/238 |
| D. 358,888 | 5/1995 | Kanas | D24/180 |
| 2,823,455 | 2/1958 | Sprague | 433/93 |
| 3,090,122 | 5/1963 | Erickson | 433/93 |
| 3,924,333 | 12/1975 | Erickson | 433/93 |
| 4,354,837 | 10/1982 | Moore | 433/91 |
| 4,802,851 | 2/1989 | Rhoades | 433/93 |
| 4,975,057 | 12/1990 | Dyfvermark | 433/93 |
| 5,009,595 | 4/1991 | Osborn | 433/140 |
| 5,232,362 | 8/1993 | Kanas | 433/93 |

Primary Examiner—John J. Wilson
Attorney, Agent, or Firm—A. Jose Cortina; R. Todd Morgan; Kilpatrick Stockton LLP

[57] ABSTRACT

A dental appliance is made up of an elongated body having a substantially longitudinal axis with opposite end portions making up substantially flat surfaces extending laterally the axis for being engaged by teeth or endentulous areas of the upper and lower jaws of a patient. A circular opening is provided with in this middle region of the elongated body to allow the tube of a saliva and debris ejector to be positioned slidably therein, and within the mouth of a patient when the apparatus is being used. The elongated body is narrower between the flat surfaces of the bite pads for maximizing the visual field of a mouth to the person performing a dental procedure. The elongated body is deformable to ensure stable engagement between the teeth or endentulous region of the upper and lower jaws of a patient and the corresponding flat surface making up the bite pads of the elongated body.

12 Claims, 3 Drawing Sheets

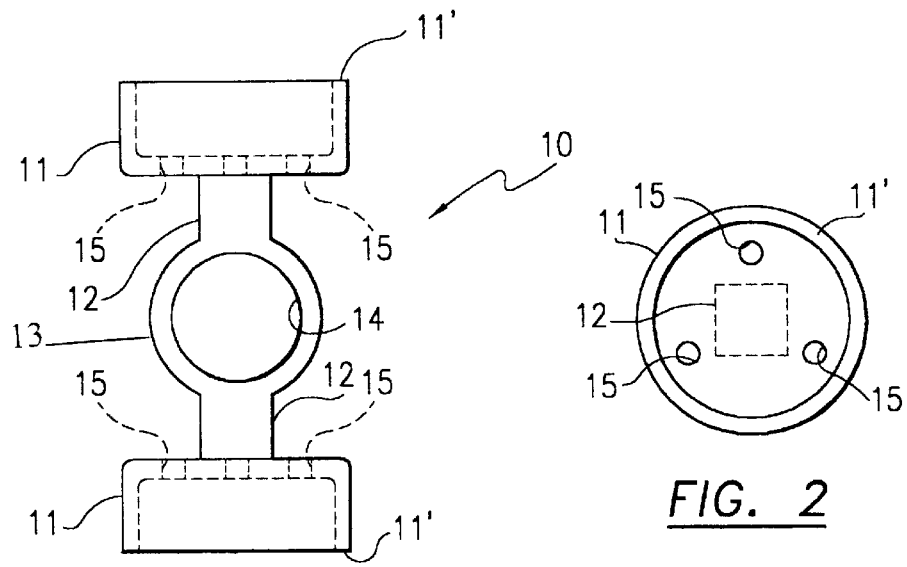
FIG. 1
FIG. 2
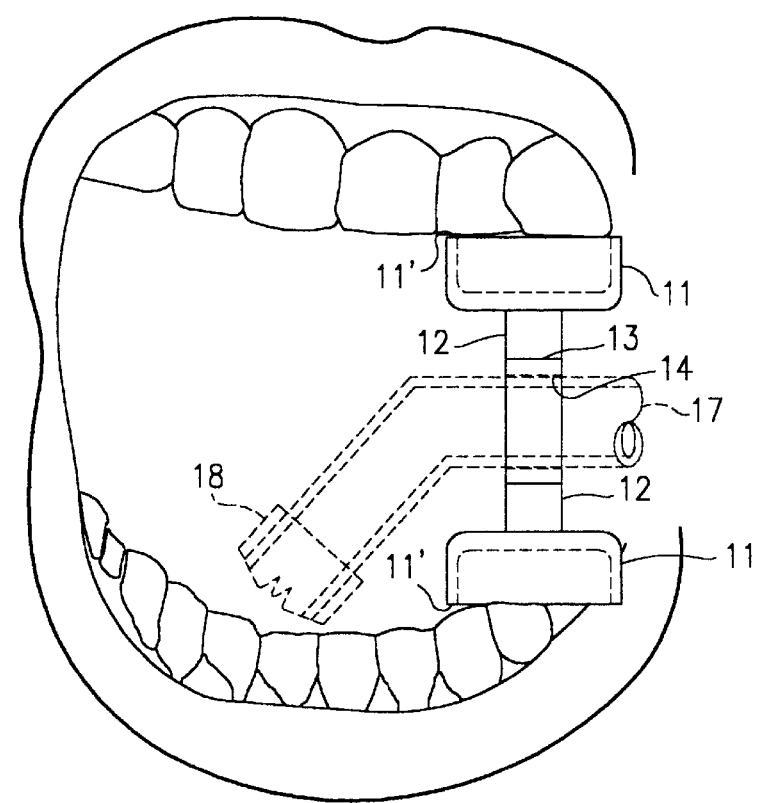
FIG. 3

5,924,866

SALIVA EJECTOR BITE BLOCK

CROSS REFERENCE TO RELATED INVENTIONS

This application is a continuation-in-part of application Ser. No. 08/805,135, filed Feb. 24, 1997, now U.S. Pat. No. 5,769,635.

BACKGROUND OF THE INVENTION

1. Field of the Invention

The present invention pertains to dental appliances and particularly to removable saliva ejector biting blocks and mouth rests.

2. Discussion of the Prior Art

Bite blocks used as mouth rests are well known to dentistry. The devices, however, tend to be physically large and cumbersome and the devices tend to obstruct the view of the mouth—"the working field"—of the dental professional. In addition, many of the devices are not easily usable by a dental professional who is working without an assistant and they are not very stable in cooperation with lip, tongue and gag reflexes. Oftentimes, due to these limitations, the saliva ejector is not always positioned for optimum fluid and debris removal. In addition, such devices are often made of hard materials, often posing a danger to chipping of a patient's teeth.

An example of one such prior art device includes a receptacle supported at the end of a drain tube. The drain tube has a bite block mounted thereon. The receptacle is complex in shape and the bite block is spherical and made of hard rubber mixed with clay or a like inelastic filler. As a result, the bite block can easily roll from one tooth to another in an unstable support condition.

Another prior art device includes a complex arrangement of left and right tongue guards connected to a bite block by means of a score line structure. To work on either side of a patient's mouth, one or the other tongue guard must be broken, resulting in a cumbersome device, and an unnecessary complex operation.

Yet still another prior art device provides a bite tube with a hole through which a tongue deflector/aspirator tube is passed. The bite tube is held by a patient's teeth in a manner enabling the edges of the tube to contact a patient's gums. This poses a danger of damage to the patient's gums due to the sharp edges of the tube. This configuration also blocks access to the instrumentation at gum line areas.

In accordance with the invention, the complexities and the disadvantages of the prior art are avoided. A bite block is provided which is simple to use, does not pose a danger of damage to a patient's mouth, allows workability in the area the device is positioned, is inexpensive to manufacture and can be made disposable.

SUMMARY OF THE INVENTION

In one aspect of the present invention there is provided a dental apparatus for insertion into the mouth of a patient during a dental procedure by a person. In a first embodiment the dental apparatus includes an elongated body having a longitudinal axis and opposite end portions, a pair of bite pads extending laterally of the axis and being respectively attached to the end portions for respective engagement by the upper and lower jaws of a patient. A first attaching mechanism is located generally medially of the body for removably securing a tube of a saliva and debris ejector thereto and for positioning the tube in the mouth of a patient. The body has a narrow arm extending between each pad and the first attaching mechanism to maximize visual field of a mouth to the person performing a dental procedure. Other aspects of the invention include the first attaching mechanism made up of a substantially circular ring member defining an opening through the elongated body, with the opening being sized to slidably engage a tube of an ejector. Each bite pad in this embodiment is formed of deformable material for engaging teeth of a patient. Each bite pad also has a plurality of spaced openings for drainage of fluid and debris therefrom. The ring member is generally planar in shape and dimensioned for maximizing visual field of a mouth to a person performing a dental procedure. The arm members are formed of a solid material to minimize the bending of either of the arm members when the apparatus is being used to hold a patient's mouth open.

Each bite pad is cup shaped and generally semi-hemispherical. The arm members are formed of a rigid material to resist bending of either of the arm members when the apparatus is in use. The first attaching means includes a passageway through the body member, the passageway is substantially circular in shape.

In an alternative embodiment, the dental apparatus of the invention includes an elongated body having a substantially longitudinal axis and opposite end portions. The end portions are made up of substantially flat surfaces extending laterally of the longitudinal axis for being engaged by teeth or endentulous areas of the upper and lower jaws of a patient. Similar to the first embodiment, an attaching mechanism is located on the elongated body for removably securing a tube of a saliva and debris ejector thereto, and for positioning the tube of the saliva and debris ejector in the mouth of the patient. The elongated body is narrower between the flat surfaces than at the flat surfaces for maximizing the visual field of a mouth to a person performing a dental procedure. In this embodiment the body is sufficiently deformable to ensure a stable engagement between the teeth or in endentulous region of the upper and lower jaws of a patient, and the corresponding flat surface to the elongated body, while at the same time being sufficiently rigid to ensure that the tube is not deformed when received therein and the elongated body compressed by jaw pressure.

In addition, since the device is made of foam material, fluids in the mouth are absorbed. This obviates the need for drainage holes as in the first embodiment. The fluids are then discharged in a slow, steady and controlled manner due to incremental pressure exerted by the jaw.

In a more preferred aspect, the attaching mechanism is made up of a substantially circular opening in the elongated body for slidably receiving and engaging the tube of the ejector. Preferably, the elongated body is comprised of semi-rigid polymer foam block having a shore-A durometer hardness greater than about 50, and having an opening therethrough for slidably engaging the vacuum tube of a saliva and debris ejector. The hardness is sufficient to prevent the opening from being compressed by the jaws of a patient to deform the tube of a saliva ejector received therein. Preferably the polymer foam is a bio-compatible polyolefin polymer selected from a number of homopolymers, copolymers and blends or mixtures thereof.

BRIEF DESCRIPTION OF THE DRAWINGS

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings, in which:

FIG. 1 is a front diagrammatic view of the saliva ejector bite block in accord with a first embodiment of the present invention;

FIG. 2 is an enlarged end view of the bite block of FIG. 1;

FIG. 3 is a pictorial view of the bite block of FIG. 1 placed in a patient's mouth;

DETAILED DISCUSSION OF THE INVENTION

Figure 4:
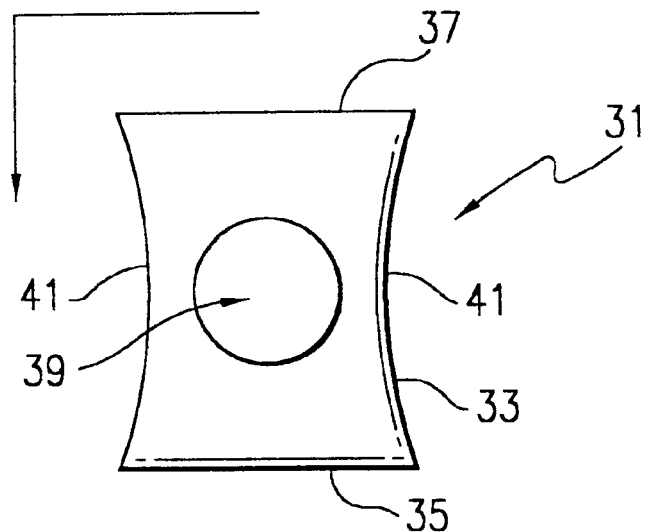
FIG. 4 is a front diagrammatic view of the saliva ejector bite block in accord with a second embodiment of the present invention.
Figure 5:
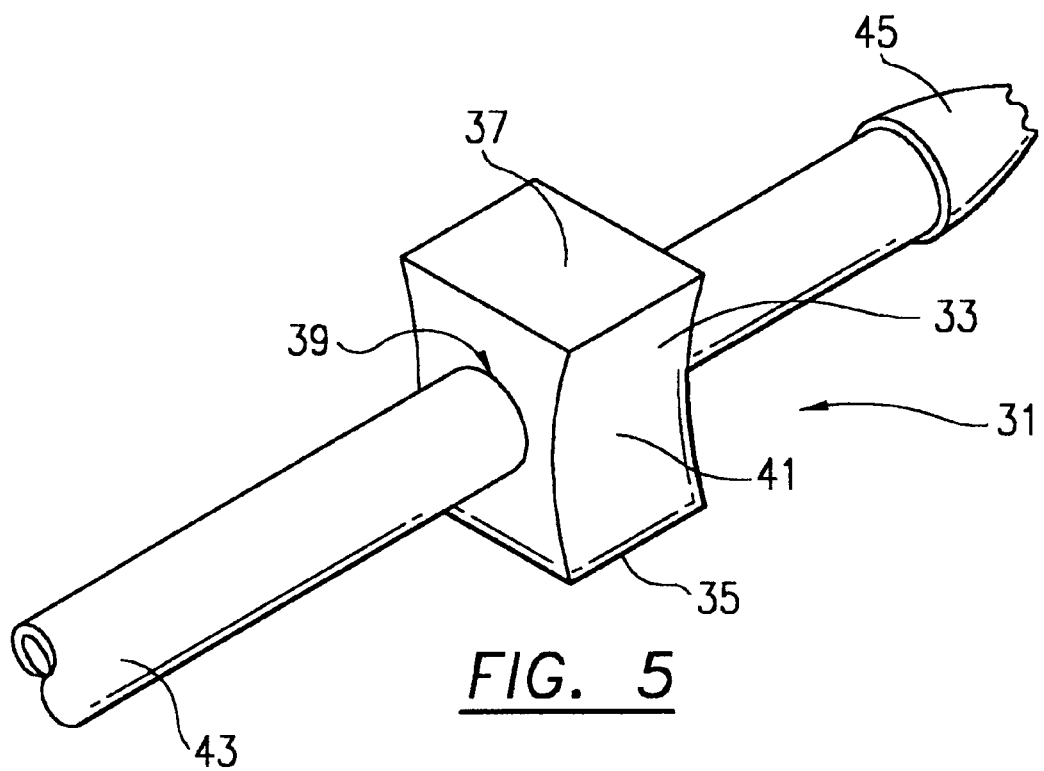
FIG. 5 is a perspective view of the saliva ejector bite block of FIG. 4.

In a first embodiment, the present invention relates to a dental appliance and more specially a mouth rest that stabilizes a saliva ejector, and a flexible hollow suction tube with a terminal cap secured to one end of the tube. The present invention is unique from all others in that it can be at the fingertips of the dental professional at all times even when it is not in use. Another unique aspect of the present device is that it allows for minimal obtrusion within the mouth thus providing a clear working field, operator ease and patient comfort. The device can be placed anywhere in the mouth such that the upper and lower dental arches come together to secure the device in place. In most cases the device will be secured by opposing teeth, but in the cases of edentulous areas the invention can be secured by the dental ridge.

The saliva ejector is the preferred oral vacuum system. It is used most exclusively by a dental professional when "two hand dentistry" is being done, and a dental professional is working alone without the help of an assistant. Lip, tongue and gag reflexes inhibit stabilization of the saliva ejector. The soft tissue of the mouth is many times vacuumed into the openings of the saliva ejector terminal cap inhibiting adequate removal of mouth fluids and debris as well as causing patient discomfort. The present device provides a means of stabilizing the saliva ejector while positioning the saliva ejector such that optimal fluid and debris removal is obtained while maintaining patient comfort.

The value and uniqueness of the device according to the present invention is its ease of use, including being at the fingertips of the dental professional at all times even when not in use, the clear working field it provides, patient comfort and low cost for disposable use. The disposability is important in avoiding cross contamination. The device is put on to the saliva ejector at the start of the procedure. The saliva ejector is then placed into the vacuum hose. The device is then secure on the saliva ejector with no chance of sliding into the mouth as the opening within the device for placement of the saliva ejector is smaller than the saliva ejector terminal cap as well as vacuum hose attachment. The invention can be kept at the vacuum hose end of the saliva ejector without hampering use of the saliva ejector until such time that the device needs to be placed within the mouth. Stabilizing the saliva ejector when needed and yet having the device out of the way when free use of the saliva ejector is preferred provides that the device is uniquely at the fingertips of the dental professional at all times.

With reference to the drawings, the bite block, according to a first embodiment the present invention is illustrated generally at numeral 10 in FIG. 1. A pair of bite pads 11, having lips 11' are attached to the ends of two elongate narrow rest arms 12 that meet at the center ring member 13. The opening 14 in the ring member 13 is sized to provide a tight fit for a flexible hollow suction tube 17 with a terminal cap (shown in broken lines) to allow the device to be moved on the ejector. Openings 15 which may be of any number and size as appropriate provide for drainage of saliva and debris from inside the bite pads 11 as shown in FIG. 2.

Rest arms 12, which are square, oval, or may be of another shape, are sized to be narrow so that they will not block the view of the dental professional as do the devices of the prior art.

FIG. 3 illustrates the use of the device with a patient 16. The device comes in several sizes to accommodate various sizes of mouths and various placement positions of the device within the mouth as may be appropriate in the circumstances. Preferably, the entire device is molded as a single piece of plastic of suitable material for dental apparatus.

With respect now to a second embodiment of the present invention, the bite block is illustrated generally at numeral 31 in FIG. 4. A pair of bite pads 35 and 37, having a substantially flat surface configuration make up the ends of an elongated body 33. The elongated body 33 is made narrow at a region 41, typically of concave shape, so that when in use with a patient maximizes the field of vision into a patient's mouth. The elongated body 33 includes means for securing a saliva and debris ejector, specifically, an opening 39 typically extending through the narrowest portion thereof to allow a saliva and debris ejector 43, with an end cap 45, to be slidably received within opening 39.

Figure 6:
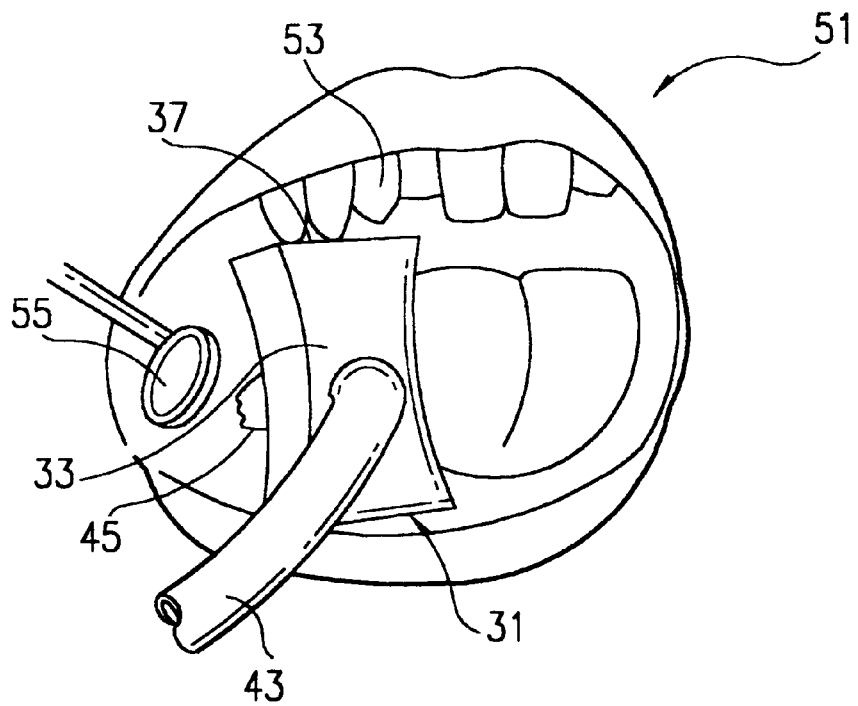
FIG. 6 is a pictorial view of the bite block of FIG. 4 placed in a patient's mouth.

As further illustrated in FIG. 6, the narrow wall portions 41 which generally give the bite block 31 a generally concave configuration along the side walls thereof permit a greater field of vision into a patient's mouth 51. As may be appreciated from FIG. 6, a conventional dental tool 55 can be used in treating the patient as the patient's teeth 53 abut against the bite pad 37 and 35 (not shown). As previously noted, the elongated body 33 is preferably made sufficiently deformable to ensure stable engagement between the teeth, or in the alternative, engagement with an endentulous region of the upper and lower jaws of a patient. Thus, the teeth or endentulous region will slightly deform bite pads 35 and 37 and ensure a locking type engagement preventing the bite block 31 from easily moving from one tooth or a portion of an endentulous region to another.

This is contrasted to one prior art device in which a typically wheel shaped member is provided, which while being somewhat deformable, emphasis is placed on the rigidity thereof, thereby facilitating rolling from one tooth to the other and creating an unstable prop situation within the mouth of a patient.

Figure 7:
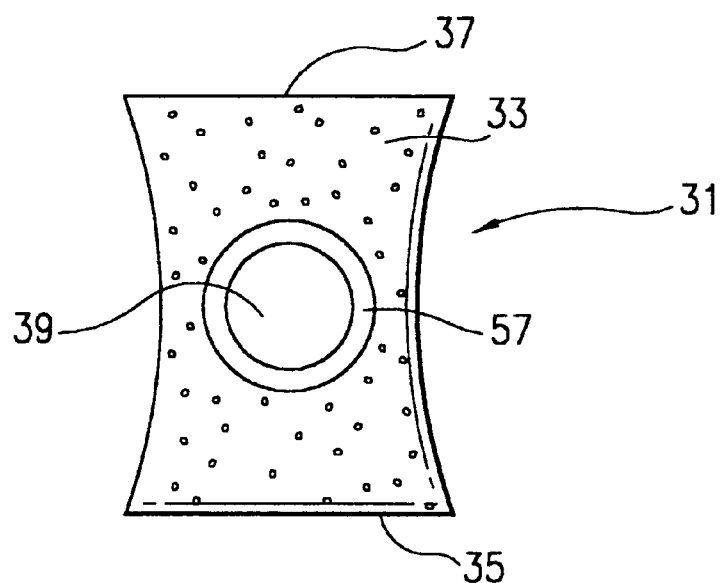
FIG. 7 is a cross-sectional view along the arrow line of FIG. 4 of the bite block of the second embodiment.

As further illustrated in FIG. 7, the elongated body 33 is preferably made of closed cell foam. Specifically, the elongated body 33 is optionally comprised of semi-rigid polymer foam block having a Shore-A durometer hardness greater than about 50 but not so great as to not allow sufficient compression to allow the body 33 to be held firmly in place.

Preferably the polymer foam block is a bio-compatible olefin polymer. By the term "bio-compatible" is meant the condition of being compatible with living tissue by virtue of lack of toxicity or ability to cause immunological rejection.

More preferably, the olefin polymer can be 1) a polyolefin homopolymer, 2) a copolymer of olefins with vinyl esters, 3) a copolymer of olyfins with vinyl alcohol, or 4) a mixture of a polyolefin homopolymer, a copolymer of olefins with vinyl esters and a copolymer of olefins with vinyl alcohol. In a more specific aspect, the olefin polymer is one of polyethylene, polypropylene, an ethylene-vinyl alcohol copolymer, an ethylene-vinyl acetate copoylmer, an ethylene-propylene copolymer, a terpolymer of ethylene, a propylene ester, a vinyl ester, or a blend or mixture of all of the foregoing. Yet still alternatively, the elongated body 33 can be made of one of zotefoam, rubber, or styrofoam. Zotefoam is a thermoplastic material made of thousands of molecular units connected into strands. The material is cross-linked. In the case of Zotefoam, it is unique in that cross-linked polyolefins (XLPO) are physically expanded with pure nitrogen in high-pressure equipment. Additional details about Zotefoam are conventional, well known and can be obtained in brochures from Zotefoams, Inc. of Hackettstown, N.J. Commercially available Zotefoams include those available under the registered trademarks, Plastazote, Evazote and Supazote. The materials are particularly suited for use in the invention due to their isotropic properties (no orientation), cellular and density consistency.

If it is desired to further rigidify the opening 39 of the elongated body 33 to ensure that a saliva and debris ejector tube received therein cannot be compressed by excessive jaw pressure, a cylindrical sleeve 57 which is rigid, for example of metal or other rigid construction, including various plastic or composite materials as will be readily apparent to those of ordinary skill in the art, can be received within the opening to protect the saliva and debris ejector tube. Alternatively, if the saliva and debris ejector tube 43 is sufficiently rigid, the elongated body 33 can be made softer while relying on the saliva and debris ejector tube 43 to help keep its shape. As a result greater deformation at the bite pads 35 and 37 occurs, resulting in more secure engagement between the pads 35 and 37 and teeth or endentulous region.

With respect to the deformability of the elongate member 33, a typical minimum hardness has been described, and for the maximum hardness it is preferred that sufficient hardness is provided to ensure that excessive deformation and/or destruction of elongate member 33 does not occur, particularly in cases where a patient is capable of extremely high jaw compression forces, but that also, sufficient deformation occurs to allow the member 33 to be held firmly in place.

It is important to appreciate that the deformability of the material for the elongated member 33 allows for very efficient tooth or endentulous region gripping of the material for retention as well as for providing comfort. Further, the deformability of the material will also allow for some compensation of size within the construction of "small", "medium" and "large" sizes, and further, allows the bite block to be made disposable.

Since saliva and debris ejector tubes come of a standard size, it is important that the opening through the bite block 31 be approximately 7 millimeters in diameter. The concave arrow region 41 allows the bite block 31 to be made of a dimension of approximately 13 millimeters allowing for great visibility into the mouth and the typical height from bite pad 35 to bite pad 37 is about 25 millimeter. The height for small, i.e., pedodontic mouths ranges from about 22 millimeters to about 24 millimeters. The standard size is typically about 24 millimeters to about 26 millimeters, and one to accommodate a wide mouth would be about 26 millimeters to about 29 millimeters.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed is:

1. A dental apparatus for insertion into the mouth of a patient during a dental procedure, comprising an elongated body having a substantially longitudinal axis and opposite end portions, said longitudinal axis of said elongated body having a midpoint located approximately between said opposite end portions, said end portions being made up of substantially flat surfaces extending laterally of said axis for being engaged by teeth or edentulous areas of the upper and lower jaws of a patient, attaching means located on said elongated body for removably securing a tube of saliva and debris ejector thereto for being positioned in the mouth of a patient, said elongated body tapering from a maximum width at the point of attachment to said end portions to a minimum width at said midpoint of said longitudinal axis of said elongated body for maximizing the visual field of a mouth to a person performing a dental procedure, and said body being sufficiently deformable to ensure a stable engagement between the teeth or edentulous region of the upper and lower jaws of a patient, and the corresponding flat surface of the elongated body, and sufficiently rigid to ensure that said tube is not deformed.

2. The dental apparatus is defined in claim 1 wherein said attaching means comprises a substantially circular opening in said elongated body for slidably engaging said tube of said ejector.

3. The dental apparatus as defined in claim 2 further comprising a tube of saliva and debris ejector for being slidably engaged in said circular opening of said elongated body, and said apparatus and circular opening being deformable out of their shape when said tube of saliva and debris is not slidably engaged therein when compressed by the jaws of a patient, and said tube of saliva and debris ejector being sufficiently rigid to prevent said apparatus and said circular opening from being deformed substantially out of its shape when received in said elongated body and compressed by the jaws of a patient.

4. The dental apparatus as defined in claim 2 wherein said circular opening is defined by a substantially rigid cylindrical insert received in said elongated body.

5. The dental apparatus as defined in claim 1 wherein said elongated body is comprised of a semi-rigid polymer foam block having a shore-A durometer hardness greater than about 50, and having an opening therethrough for slidably engaging the vacuum tube of a saliva and debris ejector, and said hardness being sufficient to prevent said opening from being compressed by the jaws of a patient to deform the tube of a saliva ejector received therein.

6. The dental apparatus as defined in claim 5 wherein said polymer foam block is a bio-compatible olefin polymer.

7. The dental apparatus as defined in claim 6 wherein said olefin polymer is one of a polyolefin homopolymer, a copolymer of olefins with vinyl esters, a copolymer of olefins with vinyl alcohol, and mixtures of a polyolefin homopolymer, a copolymer of olefins with vinyl esters and a copolymer of olefins with vinyl alcohol.

8. The dental apparatus as defined in claim 6 wherein said olefin polymer is one of polyethylene, polypropylene, an ethylene-vinyl alcohol copolymer, an ethylene-vinyl acetate copolymer, an ethylene-propylene copolymer, a terpolymer of ethylene, a propylene ester, a vinyl ester, and blends and mixtures of the foregoing.

9. The dental apparatus as defined in claim 5 wherein said elongated body is made of one of zotefoam, rubber, and styrofoam.

10. The dental apparatus as defined in claim 1 wherein said elongated body is sufficiently deformable to accommodate a variety of patient mouth cavities.

11. The dental apparatus as defined in claim 1 wherein said elongated body is no greater than about 1 mm wide at the narrowest section thereof, and said opening is of a diameter of about 7 mm.

12. The dental apparatus as defined in claim 11 wherein said elongate body is about 25 mm in length from one flat surface to the other flat surface.

* * * * *